US010351880B2

(12) United States Patent
Daviet et al.

(10) Patent No.: US 10,351,880 B2
(45) Date of Patent: Jul. 16, 2019

(54) DRIMENOL SYNTHASES I

(71) Applicant: Firmenich SA, Geneva (CH)

(72) Inventors: Laurent Daviet, Geneva (CH); Olivier Haefliger, Shanghai (CN); Xiu-Feng He, Shanghai (CN); Jian Li, Shanghai (CN); Yu-Hua Zhang, Shanghai (CN)

(73) Assignee: Firmenich SA, Geneva (CH)

( * ) Notice: Subject to any disclaimer, the term of this patent is extended or adjusted under 35 U.S.C. 154(b) by 43 days.

(21) Appl. No.: 15/330,813

(22) PCT Filed: May 6, 2015

(86) PCT No.: PCT/EP2015/059987
§ 371 (c)(1),
(2) Date: Nov. 7, 2016

(87) PCT Pub. No.: WO2015/176959
PCT Pub. Date: Nov. 26, 2015

(65) Prior Publication Data
US 2018/0208948 A1    Jul. 26, 2018

(30) Foreign Application Priority Data
May 6, 2014  (WO) ................ PCT/CN2014/076850

(51) Int. Cl.
*C12P 7/02*   (2006.01)
*C12N 9/88*   (2006.01)
(52) U.S. Cl.
CPC .................. *C12P 7/02* (2013.01); *C12N 9/88* (2013.01); *C12Y 402/03* (2013.01)

(58) Field of Classification Search
None
See application file for complete search history.

(56) References Cited

FOREIGN PATENT DOCUMENTS

WO    WO2013058654    4/2013
WO    WO2013058655    4/2013

OTHER PUBLICATIONS

Aricu. Chemistry Journal of Moldova. General, Industrial and Ecological Chemistry. 2009, 4 (2), 14-23. (Year: 2009).*
International Search Report and Written Opinion, application PCT/EP2015/059987 dated Sep. 17, 2015.
XP55211211, Jul. 2012, Retrieved from the Internet, URL: http://theses.ucalgary.ca/bitstream/11 023/129/2/ucalgary_2012_pyle_bryan.pdf.

* cited by examiner

*Primary Examiner* — Christian L Fronda
(74) *Attorney, Agent, or Firm* — Armstrong Teasdale LLP

(57) ABSTRACT

The present invention relates to a method of producing drimenol and/or drimenol derivatives by contacting at least one polypeptide with farnesyl diphosphate. The method may be performed in vitro or in vivo. The present invention also provides amino acid sequences of polypeptides useful in the method of the invention and nucleic acid encoding the polypeptides of the invention. The method further provides host cells or organisms genetically modified to express the polypeptides of the invention and useful to produce drimenol and/or drimenol derivatives.

18 Claims, 8 Drawing Sheets
Specification includes a Sequence Listing.

SEQUENCE LISTING

<160> NUMBER OF SEQ ID NOS: 11

<210> SEQ ID NO 1
<211> LENGTH: 28
<212> TYPE: DNA
<213> ORGANISM: artificial
<220> FEATURE:
<223> OTHER INFORMATION: Outer primer

<400> SEQUENCE: 1
atcttcctcc tcgtggctca ttacatcg                28

<210> SEQ ID NO 2
<211> LENGTH: 28
<212> TYPE: DNA
<213> ORGANISM: Artificial Sequence
<220> FEATURE:
<223> OTHER INFORMATION: Inner primer

<400> SEQUENCE: 2
cggccaaacg attaccgatt gacactac                28

<210> SEQ ID NO 3
<211> LENGTH: 28
<212> TYPE: DNA
<213> ORGANISM: Artificial Sequence
<220> FEATURE:
<223> OTHER INFORMATION: Outer primer

<400> SEQUENCE: 3
taccacgaac caaagtactc tccggctc                28

<210> SEQ ID NO 4
<211> LENGTH: 28
<212> TYPE: DNA
<213> ORGANISM: Artificial Sequence
<220> FEATURE:
<223> OTHER INFORMATION: Inner primer

<400> SEQUENCE: 4

```
ggaagagtta aaagctatcg ccaagtgc                                          28
```

<210> SEQ ID NO 5
<211> LENGTH: 1671
<212> TYPE: DNA
<213> ORGANISM: Valeriana amurensis

<400> SEQUENCE: 5

```
atgtctactg cattaaacag tgagcatgaa actgttcgtc cattagcaag ttttaaaccg    60
agtacatggg gcgatctttt catctcttat tctgaagata gccagcttaa ggaagtatat   120
ggtaaagagc acgaatgtct gaacaacaa gtgaaaacaa tgttgttgga tctgacaaat   180
tatagaattt cggagaaaat cgctttcata aatacgttgg agagattagg ggtatctcat   240
gagtttgaga atgagattga agggctgctt catcaaatgt tgatgctca ttctaaattc    300
caagatggca ttcaacactt tgatttgttc acattgggga tttactttag gattctcagg   360
caacatggct atagaatctc ttgtgatgtt ttcaacaagt tgaaagatag caacaatgaa   420
ttcaagaagg aacttaaaga ggacgctatt ggtttgctaa gtttgtacga agcgacacaa   480
gtaagagcac acgctgaaga aatttttagac gaagccctca ttttcacaaa ggctcaactt   540
gaatccatag ccgcaacctc gagcttaagc ccatttgtcg agaagcaaat tactcatgct   600
ttggtccaag ctctccacaa aggaatccca agagtcgaat cgcgccattt catctctgtt   660
tatgaagaag atcctgacaa aaatgatttg ttgttgaggt tctcaaagat tgattacaat   720
cttgtacaaa tgcttcacaa gcaagaattg tgccatatct caagtggtg gagagattcg   780
gagctcgaaa caaaactaac ttatgtgagg aatagagtgg cggaatgctt tttatggact   840
ctttgtgtgt accacgaacc aaagtactct ccggctcggc ttctgttagg caaactcata   900
aatatcatat cttgcactga tgacacatat gatgcgtatg gtacattaga ggaagttcag   960
atctttacag atgtcataca aaggttggat aggagttcta tggagcagct gccggattac  1020
atgaaaatcc tctacaaagc tgtccttgat cttttttgacg aagtagaagt tcagctatcg  1080
aaccatgaaa ctaataatac ttatcgtatg gcttatgcga aggaagagtt aaaagctatc  1140
gccaagtgct acgaaaagga gcacatatgg ttcagaaaat gtcacgtgcc cccattcgaa  1200
gaatatctag agaatgcggt agtgtcaatc ggtaatcgtt tggccgtacc tttttctttt  1260
ctgggaatgg atcaagtagc aggtgttgaa gcgttcgagt gggccaaaac tgatcccaaa  1320
atggtaaaat cgtgcggtaa agtcttacga cttgttgacg atgtaatgag ccacgaggag  1380
gaagatgtaa gaggacacgt ggcaacggga gtcgaatgct acatgaaaga acacggagtg  1440
agtagggaag aggccatcgt ggagttctac aagagggtcg agtacgcgtg aaggatgtg   1500
aacgaggaat ttataacgcc gaaccatctg catatcgacc tcctcaaccg cgttcttaac  1560
cttacaagaa ttgcagacgt tgtttacaag tttgaagacg gctacacgca tcccgagaag  1620
actctgaaac atcatatcat ggcgttgttc gtcgacccccg tccccatata g         1671
```

<210> SEQ ID NO 6
<211> LENGTH: 556
<212> TYPE: PRT
<213> ORGANISM: Valerian amurensis

<400> SEQUENCE: 6

```
Met Ser Thr Ala Leu Asn Ser Glu His Glu Thr Val Arg Pro Leu Ala
1               5                   10                  15

Ser Phe Lys Pro Ser Thr Trp Gly Asp Leu Phe Ile Ser Tyr Ser Glu
```

```
            20                  25                  30
Asp Ser Gln Leu Lys Glu Val Tyr Gly Lys Glu His Glu Cys Leu Lys
            35                  40                  45

Gln Gln Val Lys Thr Met Leu Leu Asp Leu Thr Asn Tyr Arg Ile Ser
    50                  55                  60

Glu Lys Ile Ala Phe Ile Asn Thr Leu Glu Arg Leu Gly Val Ser His
65                  70                  75                  80

Glu Phe Glu Asn Glu Ile Glu Gly Leu Leu His Gln Met Phe Asp Ala
                85                  90                  95

His Ser Lys Phe Gln Asp Gly Ile Gln His Phe Asp Leu Phe Thr Leu
            100                 105                 110

Gly Ile Tyr Phe Arg Ile Leu Arg Gln His Gly Tyr Arg Ile Ser Cys
            115                 120                 125

Asp Val Phe Asn Lys Leu Lys Asp Ser Asn Asn Glu Phe Lys Lys Glu
            130                 135                 140

Leu Lys Glu Asp Ala Ile Gly Leu Leu Ser Leu Tyr Glu Ala Thr Gln
145                 150                 155                 160

Val Arg Ala His Ala Glu Glu Ile Leu Asp Glu Ala Leu Ile Phe Thr
                165                 170                 175

Lys Ala Gln Leu Glu Ser Ile Ala Ala Thr Ser Ser Leu Ser Pro Phe
            180                 185                 190

Val Glu Lys Gln Ile Thr His Ala Leu Val Gln Ala Leu His Lys Gly
            195                 200                 205

Ile Pro Arg Val Glu Ser Arg His Phe Ile Ser Val Tyr Glu Glu Asp
            210                 215                 220

Pro Asp Lys Asn Asp Leu Leu Arg Phe Ser Lys Ile Asp Tyr Asn
225                 230                 235                 240

Leu Val Gln Met Leu His Lys Gln Glu Leu Cys His Ile Ser Lys Trp
                245                 250                 255

Trp Arg Asp Ser Glu Leu Glu Thr Lys Leu Thr Tyr Val Arg Asn Arg
            260                 265                 270

Val Ala Glu Cys Phe Leu Trp Thr Leu Cys Val Tyr His Glu Pro Lys
            275                 280                 285

Tyr Ser Pro Ala Arg Leu Leu Leu Gly Lys Leu Ile Asn Ile Ile Ser
            290                 295                 300

Cys Thr Asp Asp Thr Tyr Asp Ala Tyr Gly Thr Leu Glu Glu Val Gln
305                 310                 315                 320

Ile Phe Thr Asp Val Ile Gln Arg Leu Asp Arg Ser Ser Met Glu Gln
                325                 330                 335

Leu Pro Asp Tyr Met Lys Ile Leu Tyr Lys Ala Val Leu Asp Leu Phe
            340                 345                 350

Asp Glu Val Glu Val Gln Leu Ser Asn His Glu Thr Asn Asn Thr Tyr
            355                 360                 365

Arg Met Ala Tyr Ala Lys Glu Glu Leu Lys Ala Ile Ala Lys Cys Tyr
            370                 375                 380

Glu Lys Glu His Ile Trp Phe Arg Lys Cys His Val Pro Pro Phe Glu
385                 390                 395                 400

Glu Tyr Leu Glu Asn Ala Val Val Ser Ile Gly Asn Arg Leu Ala Val
                405                 410                 415

Pro Phe Ser Phe Leu Gly Met Asp Gln Val Ala Gly Val Glu Ala Phe
            420                 425                 430

Glu Trp Ala Lys Thr Asp Pro Lys Met Val Lys Ser Cys Gly Lys Val
            435                 440                 445
```

```
Leu Arg Leu Val Asp Asp Val Met Ser His Glu Glu Asp Val Arg
    450                 455                 460

Gly His Val Ala Thr Gly Val Glu Cys Tyr Met Lys Glu His Gly Val
465                 470                 475                 480

Ser Arg Glu Glu Ala Ile Val Glu Phe Tyr Lys Arg Val Glu Tyr Ala
                485                 490                 495

Trp Lys Asp Val Asn Glu Glu Phe Ile Thr Pro Asn His Leu His Ile
                500                 505                 510

Asp Leu Leu Asn Arg Val Leu Asn Leu Thr Arg Ile Ala Asp Val Val
            515                 520                 525

Tyr Lys Phe Glu Asp Gly Tyr Thr His Pro Glu Lys Thr Leu Lys His
    530                 535                 540

His Ile Met Ala Leu Phe Val Asp Pro Val Pro Ile
545                 550                 555

<210> SEQ ID NO 7
<211> LENGTH: 43
<212> TYPE: DNA
<213> ORGANISM: Artificial Sequence
<220> FEATURE:
<223> OTHER INFORMATION: Forward primer

<400> SEQUENCE: 7
aaggagatat acatatgaca aaaaaaagtt ggtgtcggtc agg            43

<210> SEQ ID NO 8
<211> LENGTH: 43
<212> TYPE: DNA
<213> ORGANISM: Artificial Sequence
<220> FEATURE:
<223> OTHER INFORMATION: Reverse primer

<400> SEQUENCE: 8
ctttaccaga ctcgagttac gccttttca tctgatcctt tgc             43

<210> SEQ ID NO 9
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is a, c, g, or t

<400> SEQUENCE: 9
gatttcaanm tkctrcaaaw gcttca                               26

<210> SEQ ID NO 10
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 10
```
gcattcrasg ccngwngcaa catgt     25

<210> SEQ ID NO 11
<211> LENGTH: 1671
<212> TYPE: DNA
<213> ORGANISM: Artificial Sequence
<220> FEATURE:
<223> OTHER INFORMATION: Codon optimised sequence

<400> SEQUENCE: 11

| | | |
|---|---|---|
| atgagcaccg cgttgaactc cgagcatgaa accgtccgtc cgctggctag ctttaaaccg | 60 |
| agcacgtggg gtgacctgtt catcagctac agcgaggaca gccagctgaa agaagtgtat | 120 |
| ggtaaagagc atgaatgtct aagcaacaa gttaagacca tgctgctgga cctgacgaat | 180 |
| taccgtatca gcgagaagat tgccttcatc aatacgctgg agcgcctggg tgtttctcac | 240 |
| gagttcgaga tgaaatcga aggcctcctg catcagatgt tcgacgcgca ctccaagttt | 300 |
| caagatggca ttcagcactt tgacctgttt accctgggca tttacttccg tattttgcgc | 360 |
| cagcacggtt atcgtatctc gtgcgatgtg tttaacaagc tgaaggactc taataacgaa | 420 |
| ttcaagaaag aactgaaaga gatgcaatt ggtctgctgt ctctgtatga gcgacccaa | 480 |
| gtgcgtgccc atgcagaaga gattttggac gaagcgctga tcttcaccaa ggctcagctg | 540 |
| gagagcatcg cggcgacgag cagcctgagc ccgtttgtcg agaaacagat tacccacgcc | 600 |
| ttggtgcaag cgttgcataa aggcatccca cgcgtggaga gccgccactt cattagcgtg | 660 |
| tacgaagagg acccggacaa gaacgatttg ctgctgcgtt tttccaagat tgactacaat | 720 |
| ttagttcaaa tgctgcacaa acaagagttg tgtcatatta gcaaatggtg gcgtgactcc | 780 |
| gagctggaga ctaaaactga ctacgtccgt aatcgcgtgg cagagtgttt tctgtggacc | 840 |
| ctgtgtgttt accacgagcc gaagtatagc ccggcacgtc tgctgctggg taaactgatc | 900 |
| aacatcattt cttgcacgga cgacacctat gatgcatacg gtacgctgga agaagtccaa | 960 |
| atctttaccg acgtgatcca gcgtttggac cgtagctcga tggagcagct gccggattac | 1020 |
| atgaagattc tgtataaagc tgttctggat ctgttcgatg aagttgaggt tcagctgagc | 1080 |
| aaccatgaga ctaacaatac ctaccgcatg gcgtacgcaa agaagaact gaaggctatt | 1140 |
| gcgaaatgct acgagaaaga gcacatctgg tttcgcaagt gtcatgttcc accgttcgaa | 1200 |
| gagtatctgg agaacgccgt ggtgagcatc ggtaatcgtc tggcggtccc gttcagcttc | 1260 |
| ttgggtatgg accaggttgc gggcgtcgag gcctttgagt gggcaaagac cgatcctaaa | 1320 |
| atggttaaaa gctgcggtaa ggttctgcgc ctggtcgatg atgtcatgag ccatgaagaa | 1380 |
| gaagatgtgc gtggtcacgt ggcgacgggc gttgagtgct acatgaaaga gcacggtgtc | 1440 |
| agccgtgaag aggcgatcgt tgaattctat aagcgtgtcg agtatgcatg gaaagacgtc | 1500 |
| aacgaagagt tcattactcc gaatcacttg cacattgatc tgctgaaccg tgttctgaac | 1560 |
| ttaacccgca ttgccgatgt cgtatacaag tttgaagatg ctataccca cccggaaaag | 1620 |
| acgctgaaac accatatcat ggcgctgttc gtggacccgg tgccgatcta a | 1671 |

DRIMENOL SYNTHASES I

RELATED APPLICATIONS

This application is a national stage application under 35 U.S.C. § 371 filing of International Patent Application PCT/EP2015/059987, filed May 6, 2015, which claims the benefit of Patent Application PCT/CN2014/076850, filed May 6, 2014.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 9090US_SequenceListing. The size of the text file is 12 KB, and the text file was created on Nov. 13, 2018.

TECHNICAL FIELD

The field relates to a method of producing drimenol, said method comprising contacting a polypeptide with farnesyl pyrophosphate (FPP). In particular, said method may be carried out in vitro or in vivo to produce drimenol, a very useful compound in the fields of perfumery. Also provided herein is an amino acid sequence of a polypeptide useful in the methods provided herein. A nucleic acid encoding the polypeptide of an embodiment herein and an expression vector containing said nucleic acid are provided herein. A non-human host organism or a cell transformed to be used in the method of producing drimenol is also provided herein.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms, respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified.

Biosynthetic production of terpenes involves enzymes called terpene synthases. There is virtually an infinity of sesquiterpene synthases present in the plant kingdom, all using the same substrate (farnesyl pyrophosphate, FPP) but having different product profiles. Genes and cDNAs encoding sesquiterpene synthases have been cloned and the corresponding recombinant enzymes characterized.

Currently the main sources for drimenol are plants naturally containing drimenol and the contents of drimenol in these natural sources are low. Chemical synthesis approaches have been developed but are still complex and not cost-effective.

SUMMARY

Provided herein is a method of producing drimenol comprising:
i) contacting an acyclic farnesyl diphospate (FPP) precursor with a polypeptide having drimenol synthase activity and comprising SEQ ID NO: 6 to produce the drimenol; and
ii) optionally isolating the drimenol.

Also provided herein is an isolated polypeptide having drimenol synthase activity comprising SEQ ID NO: 6.

Further provided herein is an isolated nucleic acid molecule encoding the polypeptide recited in claim 4.

Figure 1:
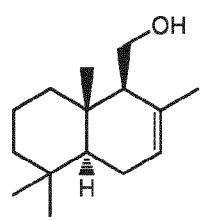
FIG. 1. Structure of (−)-drimenol

For the descriptions herein and the appended claims, the use of "or" means "and/or" unless stated otherwise. Similarly, "comprise," "comprises," "comprising", "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of." In one aspect, provided here is a method of producing drimenol comprising:
i) contacting an acyclic terpene pyrophosphate, particularly farnesyl diphospate (FPP)) with a polypeptide having drimenol synthase activity and comprising SEQ ID NO: 6 to produce rimenol; and
ii) optionally isolating the drimenol.

In one aspect, the drimenol is isolated.

In another aspect provided here, the drimenol is produced with greater than or equal to, 60%, 80%, or 90% or even 95% selectivity.

Further provided here is an isolated polypeptide having drimenol activity comprising an amino acid of SEQ ID NO: 6.

Further provided herein is an isolated nucleic acid molecule encoding a polypeptide comprising an amino acid sequence of SEQ ID NO: 6.

Further provided herein a nucleic acid molecule comprising the sequence SEQ ID NO: 5.

Further provided here is a method as recited in claim 1 comprising the steps of transforming a host cell or non-human organism with a nucleic acid encoding a polypeptide comprising SEQ ID NO: 6 and culturing the host cell or organism under conditions that allow for the production of the polypeptide.

Further provided is at least one vector comprising the nucleic acid molecules described.

Further provided herein is a vector selected from the group of a prokaryotic vector, viral vector and a eukaryotic vector.

Further provided here is a vector that is an expression vector.

As a "Drimenol synthase" or as a "polypeptide having a drimenol synthase activity", we mean here a polypeptide capable of catalyzing the synthesis of drimenol, in the form of any of its stereoisomers or a mixture thereof, starting from an acyclic terpene pyrophosphate, particularly FPP. Drimenol may be the only product or may be part of a mixture of sesquiterpenes.

The ability of a polypeptide to catalyze the synthesis of a particular sesquiterpene (for example drimenol) can be simply confirmed by performing the enzyme assay as detailed in Examples 2 to 4.

According to the present invention, polypeptides are also meant to include truncated polypeptides provided that they keep their drimenol synthase activity.

As intended herein below, "a nucleotide sequence obtained by modifying SEQ ID NO: 5 or the complement thereof" encompasses any sequence that has been obtained by changing the sequence of SEQ ID NO: 5, or of the complement thereof using any method known in the art, for example by introducing any type of mutations such as deletion, insertion or substitution mutations. Examples of such methods are cited in the part of the description relative to the variant polypeptides and the methods to prepare them.

Abbreviations Used bp base pair
kb kilo base
BSA bovine serum albumin
DNA deoxyribonucleic acid
cDNA complementary DNA
DTT dithiothreitol
FID Flame ionization detector
FPP farnesyl pyrophosphate
GC gas chromatograph
IPTG isopropyl-D-thiogalacto-pyranoside
LB lysogeny broth
MS mass spectrometer/mass spectrometry
MVA mevalonic acid
PCR polymerase chain reaction
RMCE recombinase-mediated cassette exchange
3'-/5'-RACE 3' and 5' rapid amplification of cDNA ends
RNA ribonucleic acid
mRNA messenger ribonucleic acid
miRNA micro RNA
siRNA small interfering RNA
rRNA ribosomal RNA
tRNA transfer RNA The term "polypeptide" means an amino acid sequence of consecutively polymerized amino acid residues, for instance, at least 15 residues, at least 30 residues, at least 50 residues. In some embodiments of an embodiment herein, a polypeptide comprises an amino acid sequence that is an enzyme, or a fragment, or a variant thereof.

The term "isolated" polypeptide refers to an amino acid sequence that is removed from its natural environment by any method or combination of methods known in the art and includes recombinant, biochemical and synthetic methods.

The term "protein" refers to an amino acid sequence of any length wherein amino acids are linked by covalent peptide bonds, and includes oligopeptide, peptide, polypeptide and full length protein whether naturally occurring or synthetic.

The terms "drimenol synthase" or "drimenol synthase protein" refer to an enzyme that is capable of converting farnesyl diphosphate (FPP) to drimenol.

The terms "biological function," "function," "biological activity" or "activity" refer to the ability of the drimenol synthase provided herein to catalyze the formation of drimenol from FPP.

The terms "nucleic acid sequence," "nucleic acid," and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U).

An "isolated nucleic acid" or "isolated nucleic acid sequence" is defined as a nucleic acid or nucleic acid sequence that is in an environment different from that in which the nucleic acid or nucleic acid sequence naturally occurs. The term "naturally-occurring" as used herein as applied to a nucleic acid refers to a nucleic acid that is found in a cell in nature. For example, a nucleic acid sequence that is present in an organism, for instance in the cells of an organism, that can be isolated from a source in nature and which has not been intentionally modified by a human in the laboratory, is naturally occurring.

"Recombinant nucleic acid sequences" are nucleic acid sequences that result from the use of laboratory methods (molecular cloning) to bring together genetic material from more than on source, creating a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002 Cold Spring Harbor Lab Press; and Sambrook et al., 1989 Cold Spring Harbor, N.Y.: Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3' non-translated sequence comprising, e.g., transcription termination sites.

A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription).

A "3' UTR" or "3' non-translated sequence" (also referred to as "3' untranslated region," or "3' end") refers to the nucleic acid sequence found downstream of the coding sequence of a gene, which comprises for example a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

"Expression of a gene" involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

"Promoter" refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of drimenol in the organism. Particularly, the nucleotide sequence encodes drimenol synthase.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The term "primer" refers to a short nucleic acid sequence that is hybridized to a template nucleic acid sequence and is used for polymerization of a nucleic acid sequence complementary to the template.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a drimenol synthase protein useful to produce drimenol. The host cell is particularly a bacterial cell, a fungal cell or a plant cell. The host cell may contain a recombinant gene according to the present invention which has been integrated into the nuclear or organelle genomes of the host cell. Alternatively, the host may contain the recombinant gene extra-chromosomally. Homologous sequences include orthologous or paralogous sequences. Methods of identifying orthologs or paralogs including phylogenetic methods, sequence similarity and hybridization methods are known in the art and are described herein.

Paralogs result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

Orthologs, or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in plants overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making plants producing drimenol synthase proteins.

An embodiment provided herein provides amino acid sequences of drimenol synthase proteins including orthologs and paralogs as well as methods for identifying and isolating orthologs and paralogs of the drimenol synthases in other organisms. Particularly, so identified orthologs and paralogs of the drimenol synthase retain drimenol synthase activity and are capable of producing drimenol starting from FPP precursors.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

"Drimenol" for purposes of this application refers to (−)-drimenol (CAS: 468-68-8).

The term "organism" refers to any non-human multicellular or unicellular organisms such as a plant, or a micro-organism. Particularly, a micro-organism is a bacterium, a yeast, an algae or a fungus. The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

The polypeptide to be contacted with an acyclic pyrophosphate, e.g. FPP, in vitro can be obtained by extraction from any organism expressing it, using standard protein or enzyme extraction technologies. If the host organism is an unicellular organism or cell releasing the polypeptide of an embodiment herein into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptide having a drimenol synthase activity, either in an isolated form or together with other proteins, for example in a crude protein extract obtained from cultured cells or microorganisms, may then be suspended in a buffer solution at optimal pH. If adequate, salts, DTf, inorganic cations and other kinds of enzymatic co-factors, may be added in order to optimize enzyme activity. The precursor FPP is added to the polypeptide suspension, which is then incubated at optimal temperature, for example between 15 and 40° C., particularly between 25 and 35° C., more particularly at 30° C. After incubation, the drimenol produced may be isolated from the incubated solution by standard isolation procedures, such as solvent extraction and distillation, optionally after removal of polypeptides from the solution.

According to another particularly embodiment, the method of any of the above-described embodiments is carried out in vivo. In this case, step a) comprises cultivating a non-human host organism or cell capable of producing FPP and transformed to express at least one polypeptide comprising an amino acid comprising SEQ ID NO: 6 and having a drimenol synthase activity, under conditions conducive to the production of drimenol.

According to a more particular embodiment, the method further comprises, prior to step a), transforming a non human organism or cell capable of producing FPP with at least one nucleic acid encoding a polypeptide comprising an amino acid comprising SEQ ID NO: 6 and having a drimenol synthase activity, so that said organism expresses said polypeptide.

These embodiments of an embodiment herein are particularly advantageous since it is possible to carry out the method in vivo without previously isolating the polypeptide. The reaction occurs directly within the organism or cell transformed to express said polypeptide.

According to a more particular embodiment at least one nucleic acid used in any of the above embodiments comprises a nucleotide sequence that has been obtained by modifying SEQ ID NO: 5 or the complement thereof. According to another embodiment, the at least one nucleic acid is isolated from a plant of the Valerianaceae family, particularly from *Valeriana amurensis*. The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells as specific objects provided herein and in the examples.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art.

To carry out an embodiment herein in vivo, the host organism or cell is cultivated under conditions conducive to the production of drimenol. Accordingly, if the host is a transgenic plant, optimal growth conditions are provided, such as optimal light, water and nutrient conditions, for example. If the host is a unicellular organism, conditions conducive to the production of drimenol may comprise addition of suitable cofactors to the culture medium of the host. In addition, a culture medium may be selected, so as to maximize drimenol synthesis. Optimal culture conditions are described in a more detailed manner in the following Examples.

Non-human host organisms suitable to carry out the method of an embodiment herein in vivo may be any non-human multicellular or unicellular organisms. In a particular embodiment, the non-human host organism used to carry out an embodiment herein in vivo is a plant, a prokaryote or a fungus. Any plant, prokaryote or fungus can be used. Particularly useful plants are those that naturally produce high amounts of terpenes. In a more particular embodiment the non-human host organism used to carry out the method of an embodiment herein in vivo is a microorganism. Any microorganism can be used but according to an even more particular embodiment said microorganism is a bacteria or yeast. Most particularly, said bacteria is *Escherichia coli* and said yeast is *Saccharomyces cerevisiae*.

Some of these organisms do not produce FPP naturally. To be suitable to carry out the method of an embodiment herein, these organisms have to be transformed to produce said precursor. They can be so transformed either before the modification with the nucleic acid described according to any of the above embodiments or simultaneously, as explained above.

Isolated higher eukaryotic cells can also be used, instead of complete organisms, as hosts to carry out the method of an embodiment herein in vivo. Suitable eukaryotic cells may be any non-human cell, but are particularly plant or fungal cells.

In another particular embodiment, the polypeptide comprises SEQ ID NO: 6.

According to another particular embodiment, the at least one polypeptide having a Drimenol synthase activity used in any of the above-described embodiments or encoded by the nucleic acid used in any of the above-described embodiments comprises an amino acid sequence that is a variant of SEQ ID NO: 6, obtained by genetic engineering, provided that said variant keeps its Drimenol synthase activity, as defined above and has the required percentage of identity to SEQ ID NO: 6. In other terms, said polypeptide particularly comprises an amino acid sequence encoded by a nucleotide sequence that has been obtained by modifying SEQ ID NO: 5 or the complement thereof. According to a more particular embodiment, the at least one polypeptide having a Drimenol synthase activity used in any of the above-described embodiments or encoded by the nucleic acid used in any of the above-described embodiments consists of an amino acid sequence that is a variant of SEQ ID NO: 6, obtained by genetic engineering, i.e. an amino acid sequence encoded by a nucleotide sequence that has been obtained by modifying SEQ ID NO: 5 or the complement thereof.

According to another particular embodiment, the at least one polypeptide having a Drimenol synthase activity used in any of the above-described embodiments or encoded by the nucleic acid used in any of the above-described embodiments is a variant of SEQ ID NO: 6 that can be found naturally in other organisms, such as other plant species, provided that it keeps its Drimenol synthase activity.

As used herein, the polypeptide is intended as a polypeptide or peptide fragment that encompasses the amino acid sequences identified herein, as well as truncated or variant polypeptides, provided that they keep their Drimenol synthase activity as defined above and that they share at least the defined percentage of identity with the corresponding fragment of SEQ ID NO: 6.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of an embodiment herein. Polypeptides encoded by a nucleic acid obtained by natural or artificial mutation of a nucleic acid of an embodiment herein, as described thereafter, are also encompassed by an embodiment herein.

Polypeptide variants resulting from a fusion of additional peptide sequences at the amino and carboxyl terminal ends can also be used in the methods of an embodiment herein. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of an embodiment herein.

According to another embodiment, the at least one polypeptide having a drimenol synthase activity used in any of the above-described embodiments or encoded by the nucleic acid used in any of the above-described embodiments is isolated from a plant of the Valerianaceae family, particularly from *Valeriana amurensis* An important tool to carry out the method of an embodiment herein is the polypeptide itself. A polypeptide having a drimenol synthase activity and comprising an amino acid sequence of SEQ ID NO: 6 is therefore provided herein.

According to a particular embodiment, the polypeptide is capable of producing a mixture of sesquiterpenes wherein drimenol represents at least 20%, particularly at least 30%, particularly at least 35%, particularly at least 90%, particularly at least 95%, more particularly at least 98% of the sesquiterpenes produced. In another aspect provided here, the drimenol is produced with greater than or equal to 95%, more particularly 98% selectivity.

According to a particular embodiment, the polypeptide comprises an amino acid sequence of SEQ ID NO: 6.

According to another particular embodiment, the polypeptide consists of SEQ ID NO: 6.

The at least one polypeptide comprises an amino acid sequence that is a variant of SEQ ID NO: 6, either obtained by genetic engineering or found naturally in *Valeriana* plants or in other plant species.

In other terms, when the variant polypeptide is obtained by genetic engineering, said polypeptide comprises an amino acid sequence encoded by a nucleotide sequence that has been obtained by modifying NO: 5 or the complement thereof. According to a more particular embodiment, the at least one polypeptide having a drimenol synthase activity consists of an amino acid sequence that is a variant of SEQ ID NO: 6 obtained by genetic engineering, i.e. an amino acid sequence encoded by a nucleotide sequence that has been obtained by modifying NO: 6.

According to another embodiment, the polypeptide is isolated from a plant of the Valerianaceae family, particularly from *Valeriana amurensis*. As used herein, the polypeptide is intended as a polypeptide or peptide fragment that encompasses the amino acid sequence identified herein, as well as truncated or variant polypeptides, provided that they keep their activity as defined above and that they share at least the defined percentage of identity with the corresponding fragment of SEQ ID NO: 6.

As mentioned above, the nucleic acid encoding the polypeptide of an embodiment herein is a useful tool to modify non-human host organisms or cells intended to be used when the method is carried out in vivo.

A nucleic acid encoding a polypeptide according to any of the above-described embodiments is therefore also provided herein.

According to a more particular embodiment, the nucleic acid comprises SEQ ID NO: 5 or the complement thereof.

According to another particular embodiment, the nucleic acid consists of a nucleotide sequence SEQ ID NO: 5 or the complement thereof.

The nucleic acid of an embodiment herein can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid.

Nucleic acids of an embodiment herein also encompass certain isolated nucleotide sequences including those that are substantially free from contaminating endogenous material. The nucleic acid of an embodiment herein may be truncated, provided that it encodes a polypeptide encompassed by the present invention, as described above.

In one embodiment, the nucleic acid of an embodiment herein can be either present naturally in plants of the *Valeriana* species or other species, or be obtained by modifying SEQ ID NO: 5 or the complement thereof.

The nucleic acids comprising a sequence obtained by mutation of SEQ ID NO: 5 or the complement thereof are encompassed by an embodiment herein, provided that the sequences they comprise share at least the defined sequence of SEQ ID NO: 5 or the complement thereof and provided that they encode a polypeptide having a drimenol synthase activity, as defined in any of the above embodiments. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by particular codons.

Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the drimenol synthase may be optimized for increased expression in the host cell. For example, nucleotides of an embodiment herein may be synthesized using codons particular by a host for improved expression.

Another important tool for transforming host organisms or cells suitable to carry out the method of an embodiment herein in vivo is an expression vector comprising a nucleic acid according to any embodiment of an embodiment herein. Such a vector is therefore also provided herein.

The expression vectors provided herein may be used in the methods for preparing a genetically transformed host organism and/or cell, in host organisms and/or cells harboring the nucleic acids of an embodiment herein and in the methods for making polypeptides having a drimenol synthase activity, as disclosed further below.

Recombinant non-human host organisms and cells transformed to harbor at least one nucleic acid of an embodiment herein so that it heterologously expresses or over-expresses at least one polypeptide of an embodiment herein are also very useful tools to carry out the method of an embodiment herein.

Such non-human host organisms and cells are therefore provided herein.

A nucleic acid according to any of the above-described embodiments can be used to transform the non-human host organisms and cells and the expressed polypeptide can be any of the above-described polypeptides.

Non-human host organisms of an embodiment herein may be any non-human multicellular or unicellular organisms. In a particular embodiment, the non-human host organism is a plant, a prokaryote or a fungus. Any plant, prokaryote or fungus is suitable to be transformed according to the methods described herein. Particularly useful plants are those that naturally produce high amounts of terpenes.

In a more particular embodiment the non-human host organism is a microorganism. Any microorganism is suitable as a non-human host, but according to an even more particular embodiment said microorganism is a bacterium or yeast. Most particularly, said bacterium is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Particular higher eukaryotic cells are plant cells or fungal cells.

A variant may also differ from the polypeptide of an embodiment herein by attachment of modifying groups which are covalently or non-covalently linked to the polypeptide backbone. The variant also includes a polypeptide which differs from the polypeptide provided herein by introduced N-linked or O-linked glycosylation sites, and/or an addition of cysteine residues. The skilled artisan will recognise how to modify an amino acid sequence and preserve biological activity.

The functionality or activity of any drimenol synthase protein, variant or fragment, may be determined using various methods. For example, transient or stable overexpression in plant, bacterial or yeast cells can be used to test whether the protein has activity, i.e., produces drimenol from FPP precursors.

Drimenol synthase activity may be assessed in a microbial expression system, such as the assay described in Example 2 or 3 herein on the production of drimenol, indicating functionality. A variant or derivative of a drimenol synthase polypeptide of an embodiment herein retains an ability to produce drimenol from FPP precursors. Amino acid sequence variants of the drimenol synthases provided herein may have additional desirable biological functions including, e.g., altered substrate utilization, reaction kinetics, product distribution or other alterations.

An embodiment herein provides polypeptides of an embodiment herein to be used in a method to produce drimenol contacting an FPP precursor with the polypeptides of an embodiment herein either in vitro or in vivo.

Provided herein is also an isolated, recombinant or synthetic polynucleotide encoding a polypeptide or variant polypeptide provided herein. An embodiment of an embodiment herein provides an isolated, recombinant or synthetic nucleic acid sequence of SEQ ID NO: 5 encoding for a Drimenol synthase having the amino acid sequence of SEQ ID NO: 6 or fragments thereof that catalyze production of drimenol in a cell from a FPP precursor. Provided herein are also cDNA, genomic DNA and RNA sequences. Any nucleic acid sequence encoding the drimenol synthase or variants thereof is referred herein as a drimenol synthase encoding sequence.

According to a particular embodiment, the nucleic acid of SEQ ID NO: 5 is the coding sequence of a drimenol synthase gene encoding the drimenol synthase obtained as described in the Examples.

A fragment of a polynucleotide of SEQ ID NO: 5 refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

It is clear to the person skilled in the art that genes, including the polynucleotides of an embodiment herein, can be cloned on basis of the available nucleotide sequence information, such as found in the attached sequence listing, by methods known in the art. These include e.g. the design of DNA primers representing the flanking sequences of such gene of which one is generated in sense orientations and which initiates synthesis of the sense strand and the other is created in reverse complementary fashion and generates the antisense strand. Thermo stable DNA polymerases such as those used in polymerase chain reaction are commonly used to carry out such experiments. Alternatively, DNA sequences representing genes can be chemically synthesized and subsequently introduced in DNA vector molecules that can be multiplied by e.g. compatible bacteria such as e.g. *E. coli*.

In a related embodiment provided herein, PCR primers and/or probes for detecting nucleic acid sequences encoding a drimenol synthase are provided. The skilled artisan will be aware of methods to synthesize degenerate or specific PCR primer pairs to amplify a nucleic acid sequence encoding the drimenol synthase or fragments thereof, based on SEQ ID NO: 5. A detection kit for nucleic acid sequences encoding the drimenol synthase may include primers and/or probes specific for nucleic acid sequences encoding the drimenol synthase, and an associated protocol to use the primers and/or probes to detect nucleic acid sequences encoding the drimenol synthase in a sample. Such detection kits may be used to determine whether a plant has been modified, i.e., transformed with a sequence encoding the drimenol synthase.

The nucleic acid sequences obtained by mutations of SEQ ID NO: 5 can be routinely made and are also within embodiments provided herein. It is clear to the skilled artisan that mutations, deletions, insertions, and/or substitutions of one or more nucleotides can be introduced into the DNA sequence of SEQ ID NO: 5. Generally, a mutation is a change in the DNA sequence of a gene that can alter the amino acid sequence of the polypeptide produced.

To test a function of variant DNA sequences according to an embodiment herein, the sequence of interest is operably linked to a selectable or screenable marker gene and expression of the reporter gene is tested in transient expression assays with protoplasts or in stably transformed plants. The skilled artisan will recognize that DNA sequences capable of driving expression are built as modules. Accordingly, expression levels from shorter DNA fragments may be different than the one from the longest fragment and may be different from each other. Provided herein are also functional equivalents of the nucleic acid sequence coding the drimenol synthase proteins provided herein, i.e., nucleotide sequences that hybridize under stringent conditions to the nucleic acid sequence of SEQ ID NO: 5.

The skilled artisan will be aware of methods to identify homologous sequences in other organisms and methods (identified in the Definition section herein) to determine the percentage of sequence identity between homologous sequences. Such newly identified DNA molecules then can be sequenced and the sequence can be compared with the nucleic acid sequence of SEQ ID NO: 5.

A related embodiment provided herein provides a nucleic acid sequence which is complementary to the nucleic acid sequence according to SEQ ID NO: 5 such as inhibitory RNAs, or nucleic acid sequence which hybridizes under stringent conditions to at least part of the nucleotide sequence according to SEQ ID NO: 5. An alternative embodiment of an embodiment herein provides a method to alter gene expression in a host cell. For instance, the polynucleotide of an embodiment herein may be enhanced or overexpressed or induced in certain contexts (e.g. following insect bites or stings or upon exposure to a certain temperature) in a host cell or host organism.

Alteration of expression of a polynucleotide provided herein also results in "ectopic expression" which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, several drimenol synthase encoding nucleic acid sequences are co-expressed in a single host, particularly under control of different promoters. Alternatively, several drimenol synthase protein encoding nucleic acid sequences can be present on a single transformation vector or be co-transformed at the same time using separate vectors and selecting transformants comprising both chimeric genes. Similarly, one or more drimenol synthase encoding genes may be expressed in a single plant together with other chimeric genes, for example encoding other proteins which enhance insect pest resistance, or others.

The nucleic acid sequences of an embodiment herein encoding drimenol synthase proteins can be inserted in expression vectors and/or be contained in chimeric genes inserted in expression vectors, to produce drimenol synthase proteins in a host cell or host organism. The vectors for inserting transgenes into the genome of host cells are well known in the art and include plasmids, viruses, cosmids and artificial chromosomes. Binary or co-integration vectors into which a chimeric gene is inserted are also used for transforming host cells.

An embodiment provided herein provides recombinant expression vectors comprising a nucleic acid sequence of a drimenol synthase gene, or a chimeric gene comprising a nucleic acid sequence of a drimenol synthase gene, operably linked to associated nucleic acid sequences such as, for instance, promoter sequences. For example, a chimeric gene comprising a nucleic acid sequence of SEQ ID NO: 5 or may be operably linked to a promoter sequence suitable for expression in plant cells, bacterial cells or fungal cells, optionally linked to a 3' non-translated nucleic acid sequence.

Alternatively, the promoter sequence may already be present in a vector so that the nucleic acid sequence which is to be transcribed is inserted into the vector downstream of the promoter sequence. Vectors are typically engineered to have an origin of replication, a multiple cloning site, and a selectable marker.

The following examples are illustrative only and are not intended to limit the scope of the claims an embodiments described herein.

EXAMPLES

Example 1

Figure 2:
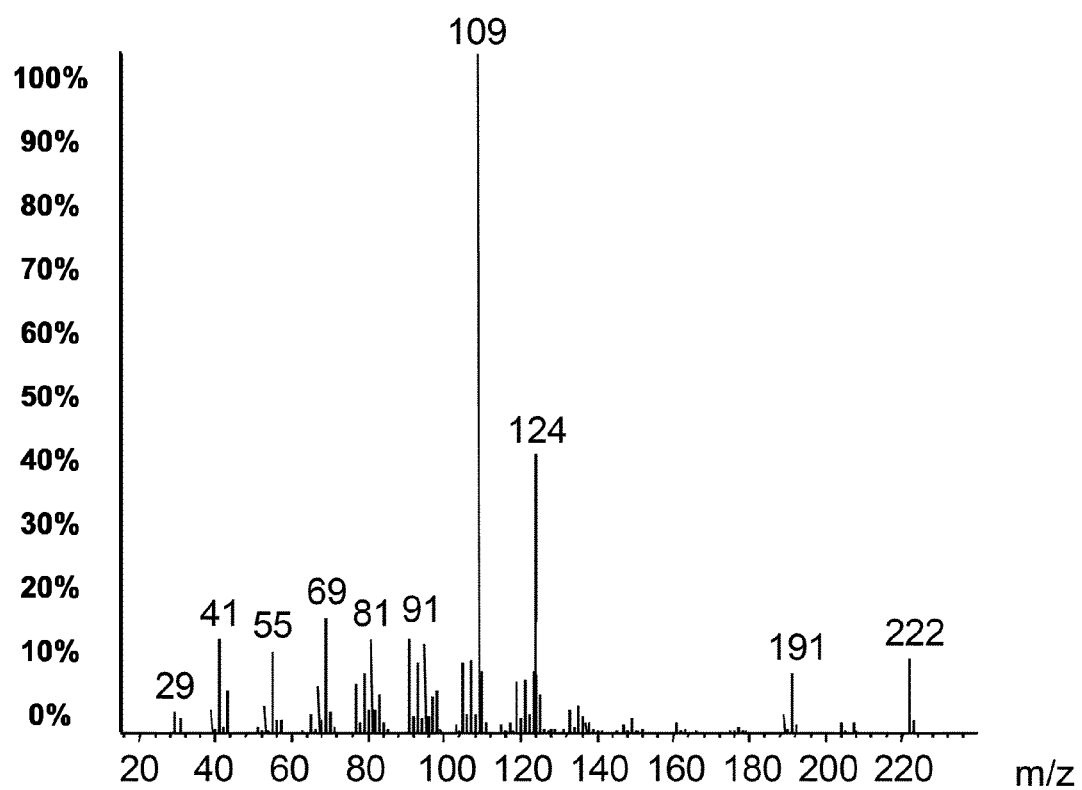
FIG. 2. Mass spectrum of authentic (−)-drimenol
Figure 3:
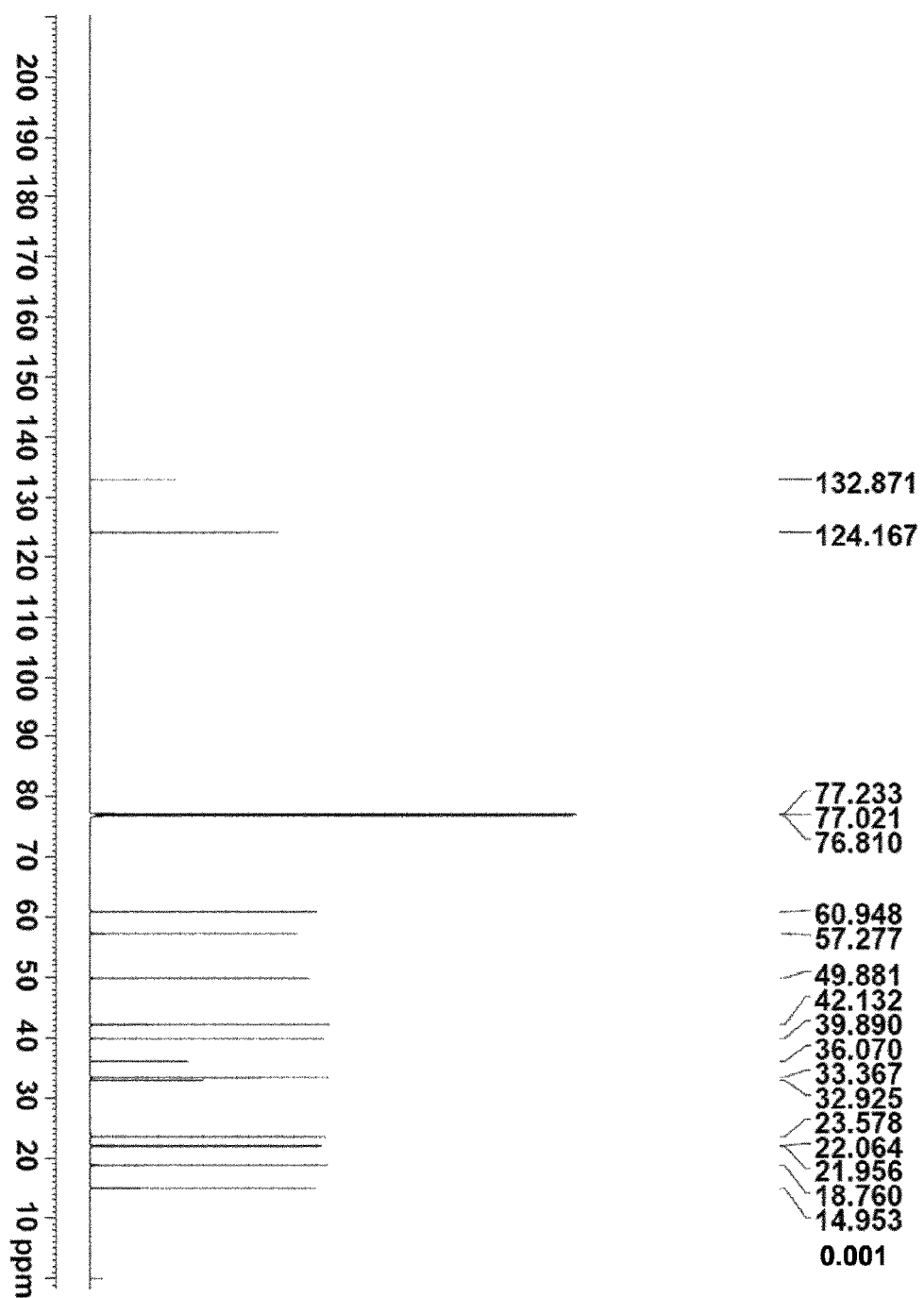
FIG. 3. $^{13}$C NMR spectrum of authentic (−)-drimenol.
Figure 4:
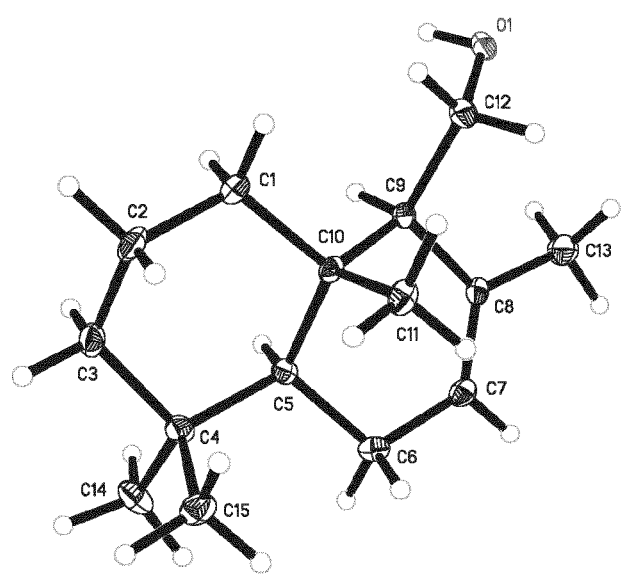
FIG. 4. X-Ray (Cu K radiation) structure of authentic (−)-drimenol

Preparation and Structure Identification of Authentic (−)-drimenol (−)-Drimenol was isolated from (*Amyris balsamifera*) by distillation followed by flash chromatography and crystallization. Structure of (−)-drimenol (FIG. 1) was identified by GC/MS (FIG. 2, LRI 1744 on DB1 column), NMR (FIG. 3), X-ray diffraction (FIG. 4), and optical rotation (−6.52°, c=0.092; MeOH).

Example 2

Isolation of a drimenol Synthase Gene (VaTPS3) from *Valeriana amurensis* and its Functional Confirmation Root tissues of living *Valeriana amurensis* plants were collected and immediately frozen in liquid nitrogen. The frozen tissues were ground into powder using mortar and pestle for RNA isolation. Total RNA was extracted using a CTAB method and treated with DNase (Ambion Turbo DNA-free DNase treatment and removal reagent) to remove DNA contaminants before cDNA synthesis. cDNA was synthesized using the Invitrogen® SuperScript III™ First-Strand Synthesis System for RT-PCR (18080-051) from total RNA by following the standard protocol recommended by the manufacturer.

For TPS gene cloning, the following degenerate primers GATITCAANMTKCTRCAAAWGCTTCA and GCAT-CRASGCCNGWNGCAACATGT were used for PCR using cDNA synthesized above as template. PCR was performed in a 20 ul reaction volume, containing 1× reaction buffer, dNTPs (0.2 mM each), primers (1 uM each), cDNA (1 ul) and DNA polymerase (0.2 ul Q5 High-Fidelity DNA polymerase, NEB). PCR parameters were as follows: 98° C. 45 seconds for initial denaturing, followed by 35 cycles of 98° C. 15 seconds, 55° C. 30 seconds and 72° C. 30 seconds. A final 72° C. for 5 minutes was added for final extension. PCR product of expected size was cloned into pMD-19-T vector for sequencing. Based on the sequence analysis, the PCR product was predicted to be a fragment of a sesquiterpene synthase gene.

The full-length of this DNA sequence was cloned by 3' and 5' RACE PCR using Clontech's SMARTer™ RACE cDNA Amplification Kit. The following gene-specific primers were used: outer primer ATCTfCCTCCTCGTGGCT-CATTACATCG and inner primer CGGCCAAACGATTAC-CGATrGACACTAC for 5' RACE; outer primer TACCACGAACCAAAGTACTCTCCGGCTC and inner primer GGAAGAGTTAAAAGCTATCGCCAAGTGC for 3' RACE. PCR products from both inner primer pairs were cloned into the pMD-19 vector by TA cloning and sequenced. The full-length sequence was then generated and was named as VaTPS3.

This full-length TPS gene was cloned into a pCAMBIA2300-based plant expression vector and its function was examined in tobacco leaves by agroinfiltration-mediated transient expression. CC/MS analysis of the treated leaves detected the presence of drimenol as the dominant volatile metabolite (up to 50 μg/g of fresh weight leaves). CC/MS was performed on an Agilent 6890 series GC system equipped with a DB1-ms column (30 m×0.25 mm id×0.25 m DB −1 ms (J&W 122-0132)) and coupled with a 5975 series mass spectrometer. The carrier gas was helium at a constant flow of 1 ml/min. Injection was in split mode (25:1) with the injector temperature set at 250° C. and the oven temperature was programmed as 50° C. (5 min hold) to 300° C. at 5° C./min, then to 340° C. at 50° C./min (3 min hold).

Figure 5:
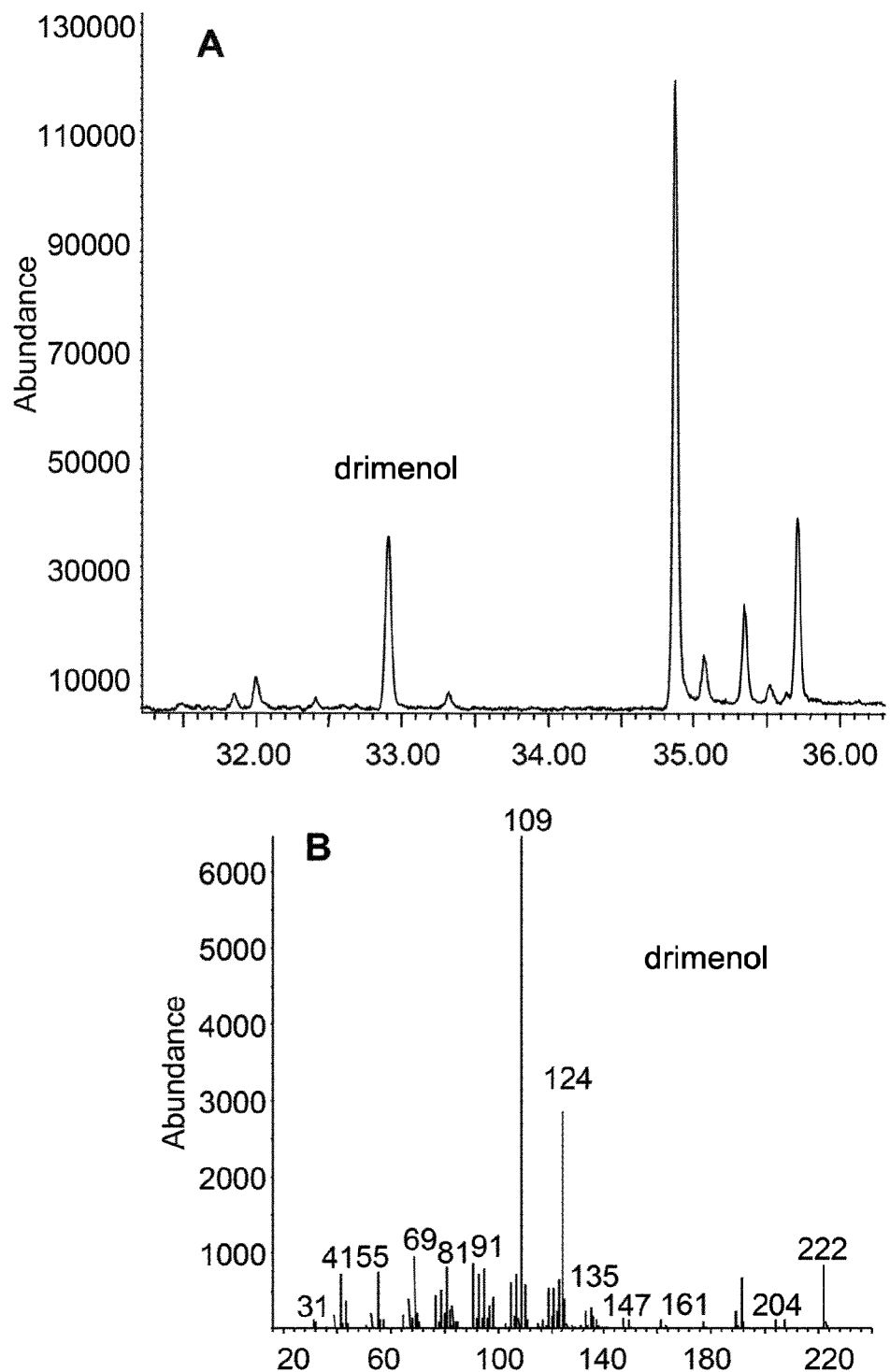
FIG. 5. GC/MS chromatogram of transient expression experiment of the isolated drimenol synthase (VaTPS3) in tobacco leaves. The drimenol peak in the GC/MS chromatogram is labeled and the corresponding mass spectrum is also provided.

The identities of the products were confirmed based on the concordance of the retention indices and mass spectra of authentic standards (FIG. 5).

GC/MS chromatogram of transient expression experiment of the isolated drimenol synthase on tobacco leaves. The drimenol peak is labelled in the GC/MS chromatogram and the corresponding mass spectrum is also displayed.

Example 3

Heterologous Expression and Functional Characterization of VaTPS3 in Engineered *E. coli* Cells For the heterologous expression of VaTPS3 in *E. coli*, a codon-optimized version of the cDNA encoding VaTPS3 was designed, synthetized by DNA2.0 (Menlo Park, Calif.) and subcloned into the pJ404 bacteria expression vector (DNA2.0) to yield pJ404/VaTPS3. *E. coli* BL21 Star™ (DE3) (Invitrogen, Carlsbad, Calif.) was used as the isoprenoid production strain. To improve in vivo productivity of the parental bacterial strain, a metabolic engineering approach via over-expression of a heterologous mevalonate pathway was undertaken. A synthetic operon consisting of an *Escherichia coli* acetoacetyl-CoA thiolase (atoB), a *Staphylococcus aureus* HMG-CoA synthase (mvaS), a *Staphylococcus aureus* HMGCoA reductase (mvaA) and a *Saccharomyces cerevisiae* farnesyl pyrophosphate (FPP) synthase (ERG20) genes were chemically synthetized by DNA2.0 and ligated into the NcoI-BamHI digested pACY-CDuet-1 vector (Invitrogen) yielding pACYC/29258. As a lower mevalonate pathway, a natural operon from *Streptococcus pneumonia* encoding for a mevalonate kinase (MvaK1), a phosphomevalonate kinase (MvaK2), a mevalonate diphosphate decarboxylase (MvaD) and an isopentenyl pyrophosphate isomerase (Fni) was PCR-amplified from genomic DNA (*S. pneumoniae* ATCC BAA-334) using the following primers: 5'-AAGGAGATATACATAT- GACAAAAAAAAGTGGTGTCGGTCAGG-3' (forward) and 5'-CTITACCAGACTCGAGTTACGCCITITCATCT-GATCCITfGC-3' (reverse). The resulting amplicon was cloned into the NdeI-XhoI digested pACYC/29258 vector using the In-Fusion 2.0 Dry-Down PCR Cloning Kit (Clontech) providing the pACYC/29258_4506 vector (*J. Am. Chem. Soc.* 2013, 134: 18900-18903). The FPP-overproducing strain was then co-transformed with the pJ404NaTPS3 construct described above. Single colonies of transformed cells were used to inoculate 5 mL of LB medium supplemented with the appropriate antibiotics. Cultures were then incubated overnight at 37° C. and 250 rpm. The following day, 2 mL of mineral 'AM' medium were inoculated with 200 µl of the overnight culture and incubated at 37° C. and 250 rpm (*J. Am. Chem. Soc.* 2013, 134: 18900-18903). After 4 to 6 hours of cultivation (or when the optical density at 600 nm of the culture reach a value of ~2), the cultures were cooled down to 25° C. and the protein expression was induced with 0.1 mM isopropyl-D-1-thiogalactopyranoside (IPTG). At that time, 10% (v/v) of dodecane was added to the growth medium. After 72 h incubation with orbital shaking (250 rpm), the cell culture was extracted twice with one volume of methyl tert-butyl ether (MTBE) and the solvent extract analyzed by GC/MS. GC/MS was performed on an Agilent 6890 series GC system equipped with a DB1 column (30 m×0.25 mm×0.25 mm film thickness; Agilent) and coupled with a 5975 series mass spectrometer. The carrier gas was helium at a constant flow of 1 ml/min. Injection was in split-less mode with the injector temperature set at 250° C. and the oven temperature was programmed from 50° C. to 225° C. at 10° C./min and to 320° C. at 20° C./min. The identities of the products were confirmed based on the concordance of the retention indices and mass spectra of authentic standards.

Figure 6:
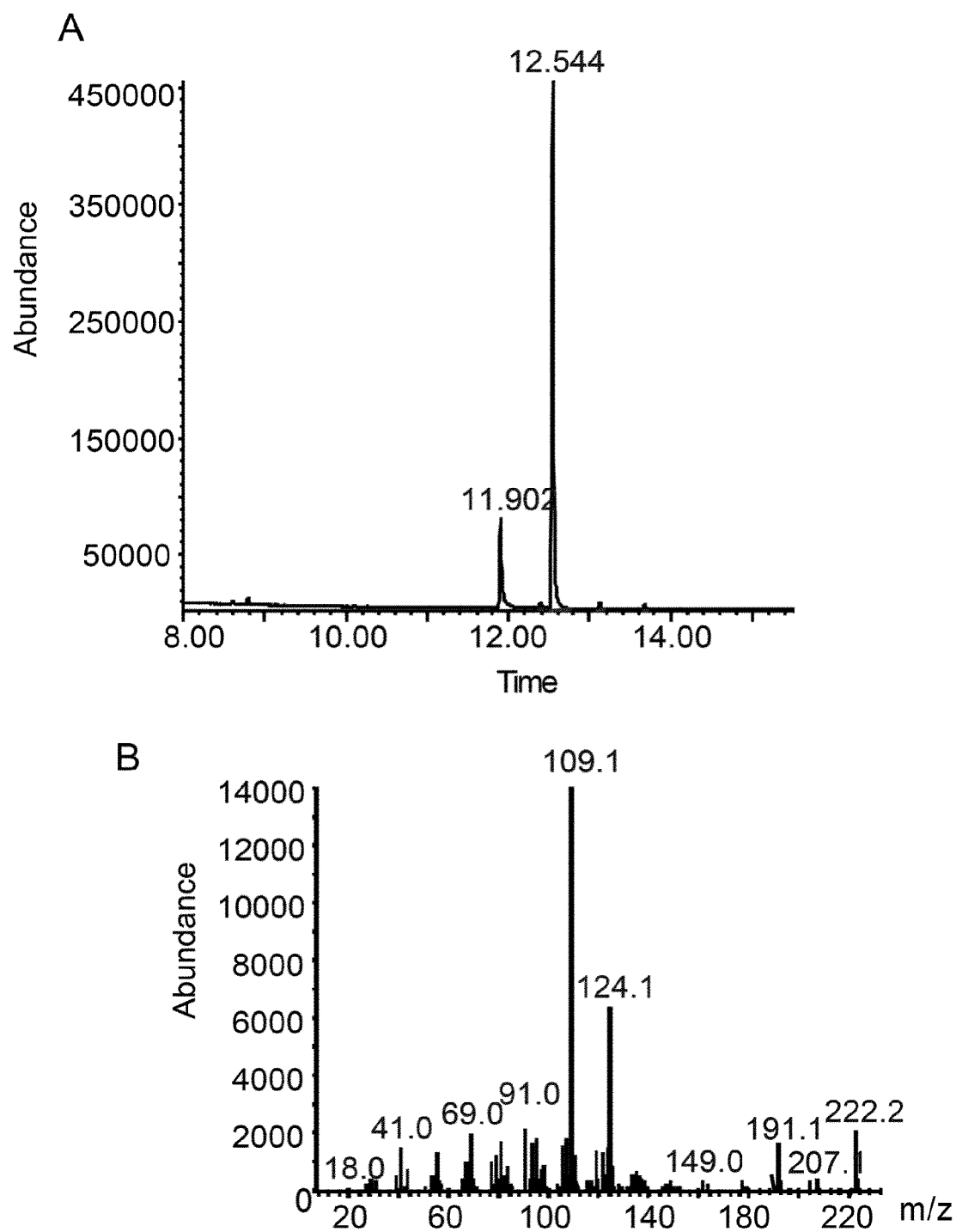
FIG. 6. GC/MS analysis of the products generated by the recombinant VaTPS3 in engineered bacterial cells. A. Total ion chromatogram of the solvent extract of the cell culture. B. GC/MS of the peak at 12.544 min (see FIG. 2 for the mass spectrum of authentic (−)-drimenol standard). The peak eluting at 11.902 min is farnesol that results from the hydrolysis of farnesyl pyrophosphate produced by the engineered E. coli cells.
Figure 7:
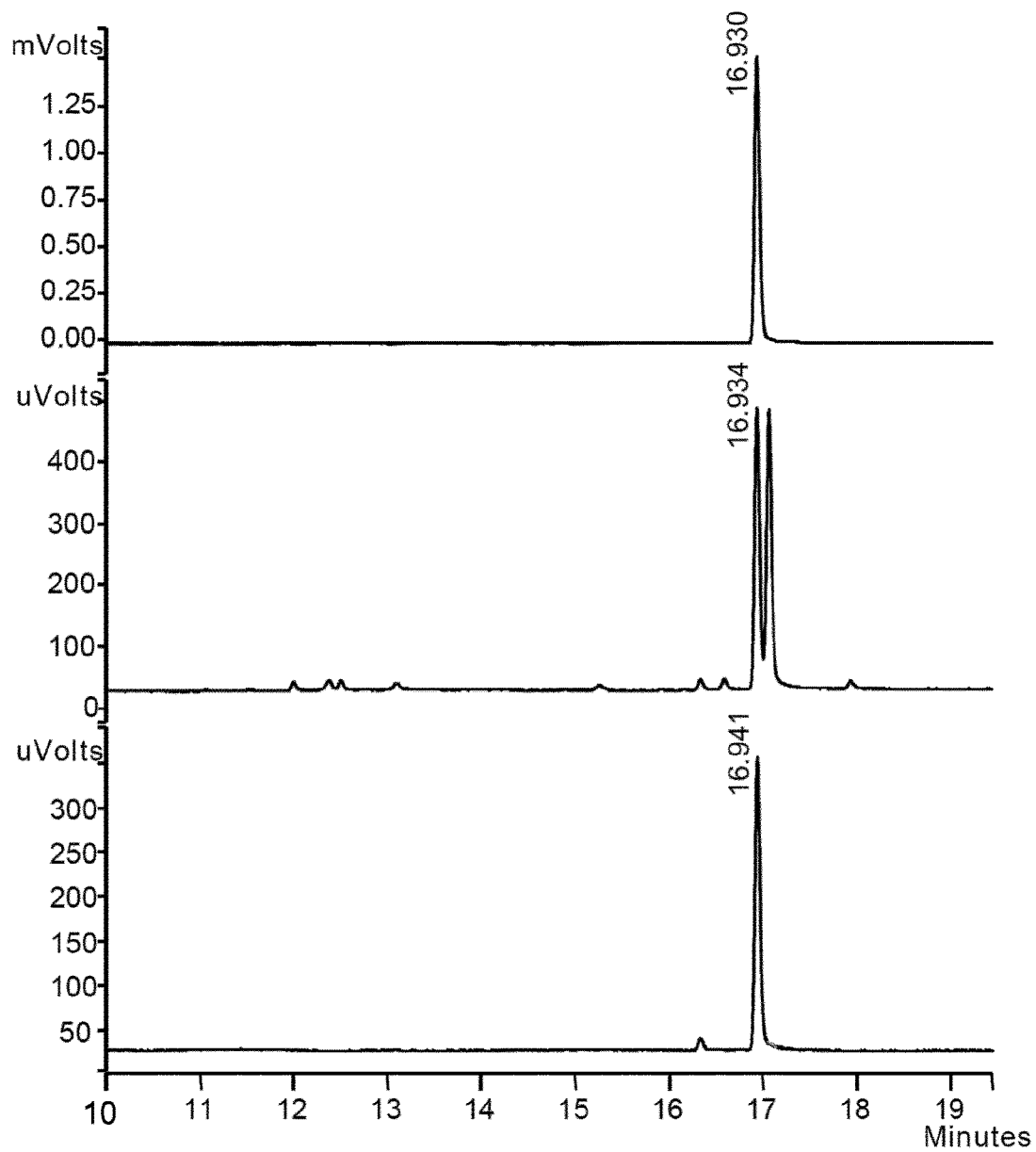
FIG. 7. Chiral GC/FID chromatograms of authentic (−)-drimenol (upper), racemic drimenol (middle), and drimenol generated by the recombinant VaTPS3 in engineered bacteria cells (lower).

As shown in FIG. 6, the recombinant VaTPS3 generated (−)-drimenol as major product (selectivity of 98%) and yielded a peak titer of about 200 mg/L. The identity of (−)-drimenol was confirmed by matching of the retention time and mass spectrum of an authentic (−)-drimenol standard isolated from (*Amyris balsamifera*). The enantiopurity was determined by chiral GC analysis (FIG. 7).

Example 4

In Vitro Functional Characterization of VaTPS3

The codon-optimized version of VaTPS3 cDNA described in Example 3 was subcloned into the pJ414 bacteria expression vector (DNA2.0) to yield pJ414/VaTPS3.

Heterologous expression of VaTPS3 was performed in BL21Star™ (DE3) *E. coli* cells (Invitrogen). Single colonies of cells transformed with the pJ414/VaTPS3 plasmid were used to inoculate 5 ml of LB medium containing 50 µg/ml of carbenicillin. After 5 to 6 hours of incubation at 37° C. under orbital shaking, the bacteria cultures were transferred to a 20° C. incubator. Expression of the recombinant VaTPS3 was then induced by the addition of 0.1 mM IPTG and the culture was incubated overnight at 20° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g) and the supernatants containing the soluble cytosolic proteins were used for further experiments.

Figure 8:
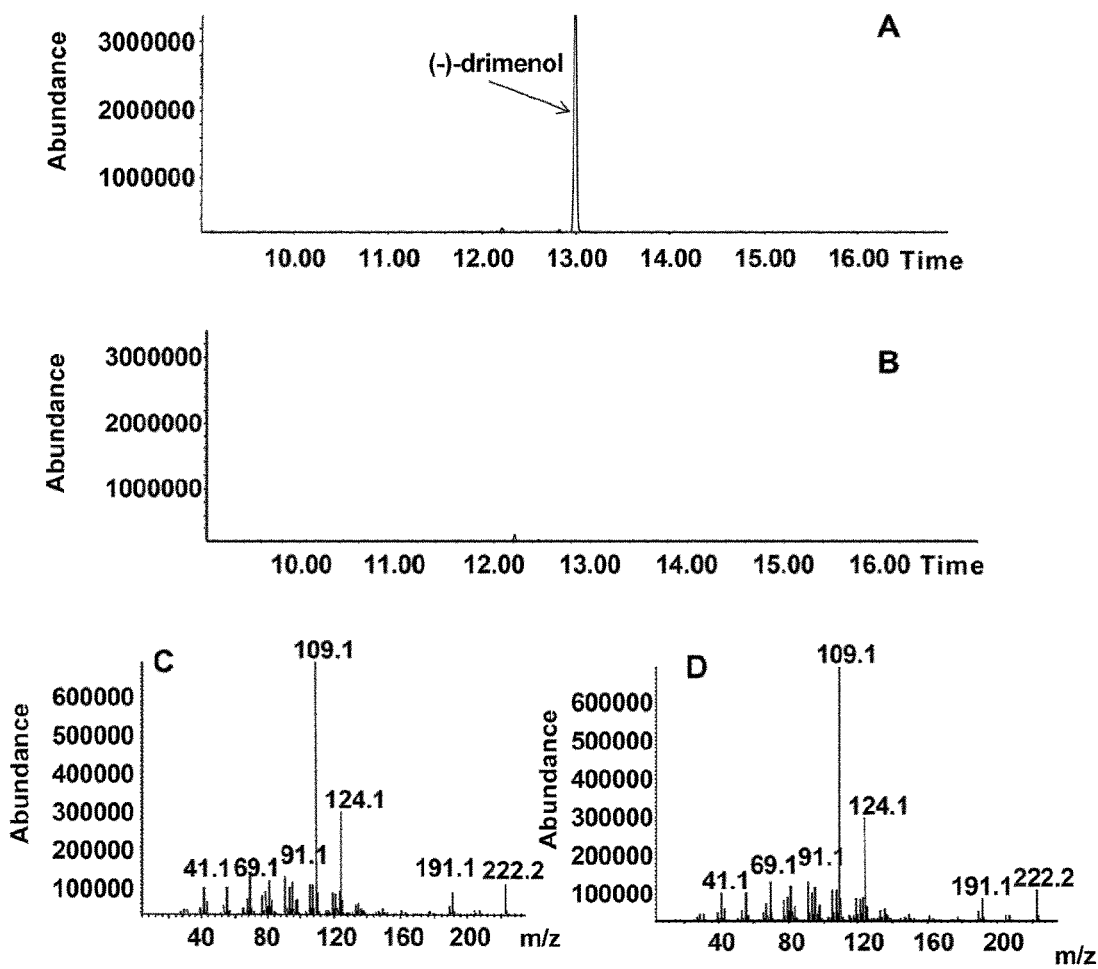
FIG. 8. GC/MS analysis of the sesquiterpenes produced in vitro by the recombinant VaTPS3 synthase. A. Total ion chromatogram of the sesquiterpenes produced by the recombinant VaTPS3 synthase when incubated with exogenous FPP. B. Negative control performed in the same experimental conditions with E. coli cells transformed with an empty plasmid. C. Mass spectrum of the peak at 12.99 min. D. Mass spectrum of an authentic (−)-drimenol standard.

The in vitro assays were performed in 1 mL of 50 mM MOPSO pH 7, 10% glycerol, 1 mM DTT, 15 mM MgCl$_2$ in the presence of 80 µM of farnesyl-diphosphate (FPP, Sigma) and 0.1 to 0.5 mg of protein extract. The tubes were incubated for 12 to 24 hours at 20° C. and extracted twice with one volume of pentane. After concentration under a nitrogen flux, the pentane extracts were analysed by GC-MS as described in example 3. A negative control was performed under the same experimental conditions using extracts of *E. coli* cells transformed with an empty pJ414 plasmid. As shown in FIG. 8, the VaTPS3 recombinant enzyme produced (−)-drimenol as major product with a selectivity over 98%. The identity of (−)-drimenol was confirmed by matching of the mass spectrum and retention time of an authentic drimenol standard isolated from (Amyris *balsamifera*).

```
                   Sequence Listings

SEQ ID NO: 1
ATCTTCCTCCTCGTGGCTCATTACATCG

SEQ ID NO: 2
CGGCCAAACGATTACCGATTGACACTAC

SEQ ID NO:3
TACCACGAACCAAAGTACTCTCCGGCTC

SEQ ID NO: 4
GGAAGAGTTAAAAGCTATCGCCAAGTGC

SEQ ID NO: 5
ATGTCTACTGCATTAAACAGTGAGCATGAAACTGTTCGTCCATTAGCAAG
TTTTAAACCGAGTACATGGGGCGATCTTTTCATCTCTTATTCTGAAGATA
GCCAGCTTAAGGAAGTATATGGTAAAGAGCACGAATGTCTGAAACAACAA
GTGAAAACAATGTTGTTGGATCTGACAAATTATAGAATTTCGGAGAAAAT
CGCTTTCATAAATACGTTGGAGAGATTAGGGGTATCTCATGAGTTTGAGA
ATGAGATTGAAGGGCTGCTTCATCAAATGTTTGATGCTCATTCTAAATTC
CAAGATGGCATTCAACACTTTGATTTGTTCACATTGGGGATTTACTTTAG
GATTCTCAGGCAACATGGCTATAGAATCTCTTGTGATGTTTTCAACAAGT
TGAAAGATAGCAACAATGAATTCAAGAAGGAACTTAAAGAGGACGCTATT
GGTTTGCTAAGTTTGTACGAAGCGACACAAGTAAGAGCACACGCTGAAGA
AATTTTAGACGAAGCCCTCATTTTCACAAAGGCTCAACTTGAATCCATAG
CCGCAACCTCGAGCTTAAGCCCATTTGTCGAGAAGCAAATTACTCATGCT
TTGGTCCAAGCTCTCCACAAAGGAATCCCAAGAGTCGAATCGCGCCATTT
CATCTCTGTTTATGAAGAAGATCCTGACAAAAATGATTTGTTGTTGAGGT
TCTCAAAGATTGATTACAATCTTGTACAAATGCTTCACAAGCAAGAATTG
TGCCATATCTCAAAGTGGTGGAGAGATTCGGAGCTCGAAACAAAACTAAC
TTATGTGAGGAATAGAGTGGCGGAATGCTTTTTATGGACTCTTTGTGTGT
ACCACGAACCAAAGTACTCTCCGGCTCCGGCTTCGTTGTTAGGCAAACTCATA
AATATCATATCTTGCACTGATGACACATATGATGCGTATGGTACATTAGA
GGAAGTTCAGATCTTTACAGATGTCATACAAAGGTTGGATAGGAGTTCTA
TGGAGCAGCTGCCGGATTACATGAAAATCCTCTACAAAGCTGTCCTTGAT
CTTTTTGACGAAGTAGAAGTTCAGCTATCGAACCATGAAACTAATAATAC
TTATCGTATGGCTTATGCGAAGGAAGAGTTAAAAGCTATCGCCAAGTGCT
ACGAAAAGGAGCACATATGGTTCAGAAAATGTCACGTGCCCCCATTCGAA
GAATATCTAGAGAATGCGGTAGTGTCAATCGGTAATCGTTTGGCCGTACC
TTTTTCTTTTCTGGGAATGGATCAAGTAGCAGGTGTTGAAGCGTTCGAGT
GGGCCAAAACTGATCCCAAAATGGTAAAATCGTGCGGTAAAGTCTTACGA
CTTGTTGACGATGTAATGAGCCACGAGGAGGAAGATGTAAGAGGACACGT
GGCAACGGGAGTCGAATGCTACATGAAAGAACACGGAGTGAGTAGGGAAG
AGGCCATCGTGGAGTTCTACAAGAGGGTCGAGTACGCGTGGAAGGATGTG
AACGAGGAATTTATAACGCCGAACCATCTGCATATCGACCTCCTCAACCG
CGTTCTTAACCTTACAAGAATTGCAGACGTTGTTTACAAGTTTGAAGACG
GCTACACGCATCCCGAGAAGACTCTGAAACATCATATCATGGCGTTGTTC
GTCGACCCCGTCCCCATATAG

SEQ ID NO: 6
MSTALNSEHETVRPLASFKPSTWGDLFISYSEDSQLKEVYGKEHECLKQQ
VKTMLLDLTNYRISEKIAFINTLERLGVSHEFENEIEGLLHQMFDAHSKF
QDGIQHFDLFTLGIYFRILRQHGYRISCDVFNKLKDSNNEFKKELKEDAI
GLLSLYEATQVRAHAEEILDEALIFTKAQLESIAATSSLSPFVEKQITHA
LVQALHKGIPRVESRHFISVYEEDPDKNDLLLRFSKIDYNLVQMLHKQEL
CHISKWWRDSELETKLTYVRNRVAECFLWTLCVYHEPKYSPARLLLGKLI
NIISCTDDTYDAYGTLEEVQIFTDVIQRLDRSSMEQLPDYMKILYKAVLD
LFDEVEVQLSNHETNNTYRMAYAKEELKAIAKCYEKEHIWFRKCHVPPFE
EYLENAVVSIGNRLAVPFSFLGMDQVAGVEAFEWAKTDPKMVKSCGKVLR
LVDDVMSHEEEDVRGHVATGVECYMKEHGVSREEAIVEFYKRVEYAWKDV
NEEFITPNHLHIDLLNRVLNLTRIADVVYKFEDGYTHPEKTLKHHIMALF
VDPVPI
```

Sequence Listings

SEQ ID NO: 7
AAGGAGATATACATATGACAAAAAAAAGTTGGTGTCGGTCAGG

SEQ ID NO: 8
CTTTACCAGACTCGAGTTACGCCTTTTTCATCTGATCCTTTGC

SEQ ID NO: 9
GATTTCAANMTKCTRCAAAWGCTTCA

SEQ ID NO: 10
GCATTCRASGCCNGWNGCAACATGT

SEQ ID NO: 11
VaTPS3 nt sequence codon-optimised (from Example 3)
ATGAGCACCGCGTTGAACTCCGAGCATGAAACCGTCCGTCCGCTGGCTAG
CTTTAAACCGAGCACGTGGGGTGACCTGTTCATCAGCTACAGCGAGGACA
GCCAGCTGAAAGAAGTGTATGGTAAAGAGCATGAATGTCTTAAGCAACAA
GTTAAGACCATGCTGCTGGACCTGACGAATTACCGTATCAGCGAGAAGAT
TGCCTTCATCAATACGCTGGAGCGCCTGGGTGTTTCTCACGAGTTCGAGA
ATGAAATCGAAGGCCTCCTGCATCAGATGTTCGACGCGCACTCCAAGTTT
CAAGATGGCATTCAGCACTTTGACCTGTTTACCCTGGGCATTTACTTCCG
TATTTTGCGCCAGCACGGTTATCGTATCTCGTGCGATGTGTTTAACAAGC
TGAAGGACTCTAATAACGAATTCAAGAAAGAACTGAAAGAAGATGCAATT
GGTCTGCTGTCTCTGTATGAAGCGACCCAAGTGCGTGCCCATGCAGAAGA
GATTTTGGACGAAGCGCTGATCTTCACCAAGGCTCAGCTGGAGAGCATCG
CGGCGACGAGCAGCCTGAGCCCGTTTGTCGAGAAACAGATTACCCACGCC
TTGGTGCAAGCGTTGCATAAAGGCATCCCACGCGTGGAGAGCCGCCACTT
CATTAGCGTGTACGAAGAGGACCCGGACAAGAACGATTTGCTGCTGCGTT
TTTCCAAGATTGACTACAATTTAGTTCAAATGCTGCACAAACAAGAGTTG
TGTCATATTAGCAAATGGTGGCGTGACTCCGAGCTGGAGACTAAACTGAC
CTACGTCCGTAATCGCGTGGCAGAGTGTTTCTGTGTGGACCCTGTGTGTTT
ACCACGAGCCGAAGTATAGCCCGGCACGTCTGCTGCTGGGTAAACTGATC
AACATCATTTCTTGCACGGACGACACCTATGATGCATACGGTACGCTGGA
AGAAGTCCAAATCTTTACCGACGTGATCCAGCGTTTGGACCGTAGCTCGA
TGGAGCAGCTGCCGGATTACATGAAGATTCTGTATAAAGCTGTTCTGGAT
CTGTTCGATGAAGTTGAGGTTCAGCTGAGCAACCATGAGACTAACAATAC
CTACCGCATGGCGTACGCAAAAGAAGAACTGAAGGCTATTGCGAAATGCT
ACGAGAAAGAGCACATCTGGTTTCGCAAGTGTCATGTTCCACCGTTCGAA
GAGTATCTGGAGAACGCCGTGGTGAGCATCGGTAATCGTCTGGCGGTCCC
GTTCAGCTTCTTGGGTATGGACCAGGTTGCGGGCGTCGAGGCCTTTGAGT
GGGCAAAGACCGATCCTAAAATGGTTAAAAGCTGCGGTAAGGTTCTGCGC
CTGGTCGATGATGTCATGAGCCATGAAGAAGAAGATGTGCGTGGTCACGT
GGCGACGGGCGTTGAGTGCTACATGAAAGAGCACGGTGTCAGCCGTGAAG
AGGCGATCGTTGAATTCTATAAGCGTGTCGAGTATGCATGGAAAGACGTC
AACGAAGAGTTCATTACTCCGAATCACTTGCACATTGATCTGCTGAACCG
TGTTCTGAACTTAACCCGCATTGCCGATGTCGTATACAAGTTTGAAGATG
GCTATACCCACCCGGAAAAGACGCTGAAACACCATATCATGGCGCTGTTC
GTGGACCCGGTGCCGATCTAA

What is claimed is:

1. A method of producing drimenol comprising:
    i) contacting an acyclic farnesyl diphosphate (FPP) with a polypeptide having drimenol synthase activity and comprising SEQ ID NO: 6 to produce the drimenol; and
    ii) ii) optionally isolating the drimenol.

2. The method as recited in claim 1 comprising contacting the drimenol with at least one enzyme to produce a drimenol derivative.

3. The method as recited in claim 1 comprising converting the drimenol to a drimenol derivative using a chemical synthesis.

4. An isolated polypeptide having drimenol synthase activity comprising SEQ ID NO: 6.

5. An isolated nucleic acid molecule encoding the polypeptide recited in claim 4.

6. The nucleic acid molecule of claim 5, wherein the nucleic acid molecule encoding the polypeptide comprises the sequence of SEQ ID NO: 5.

7. The method as recited in claim 1 comprising the steps of transforming a host cell or non-human organism with a nucleic acid encoding a polypeptide comprising SEQ ID NO: 6 and culturing the host cell or organism under conditions that allow for the production of the polypeptide.

8. A vector comprising the nucleic acid molecule of claims 6.

9. The vector of claim 8 wherein the vector is a prokaryotic vector, viral vector or a eukaryotic vector.

10. The vector of claim 8 that is an expression vector.

11. The method recited in claim 7 wherein the cell is a prokaryotic cell.

12. The method as recited in claim 7 wherein the cell is a bacterial cell.

13. The method as recited in claim 7 wherein the cell is an eukaryotic cell.

14. The method as recited in claim 7 wherein the eukaryotic cell is a yeast cell or a plant cell.

15. The vector of claim 9 that is an expression vector.

16. A non-human host organism or cell comprising the nucleic acid molecule of claim 5 or a vector comprising said nucleic acid.

17. The non-human host organism or cell of claim 16, wherein the non-human host organism or cell is a bacterium, a yeast, a fungal cell or a plant cell.

18. The non-human host organism or cell of claim 17, wherein the bacterium is *E. coli* and the yeast is *Saccharomyces cerevisiae*.

* * * * *